(12) United States Patent
Kocher et al.

(10) Patent No.: US 11,123,002 B1
(45) Date of Patent: Sep. 21, 2021

(54) BRAIN MATCHING

(71) Applicants: Robert William Kocher, McLean, VA (US); Loran Dean Ambs, Williamsburg, VA (US)

(72) Inventors: Robert William Kocher, McLean, VA (US); Loran Dean Ambs, Williamsburg, VA (US)

(*) Notice: Subject to any disclaimer, the term of this patent is extended or adjusted under 35 U.S.C. 154(b) by 0 days.

(21) Appl. No.: 16/991,292

(22) Filed: Aug. 12, 2020

Related U.S. Application Data

(63) Continuation of application No. 15/530,894, filed on Mar. 20, 2017, now Pat. No. 10,772,527.

(51) Int. Cl.
*G06N 3/02* (2006.01)
*A61B 5/291* (2021.01)
*A61B 5/00* (2006.01)
*G16H 40/63* (2018.01)
*G16H 50/20* (2018.01)
*A61B 5/38* (2021.01)
*A61B 5/378* (2021.01)
*A61B 5/381* (2021.01)
*G06N 3/08* (2006.01)
*G06Q 10/06* (2012.01)
*A61B 5/16* (2006.01)

(52) U.S. Cl.
CPC .............. *A61B 5/291* (2021.01); *A61B 5/378* (2021.01); *A61B 5/38* (2021.01); *A61B 5/381* (2021.01); *A61B 5/4064* (2013.01); *A61B 5/6814* (2013.01); *A61B 5/7246* (2013.01); *A61B 5/7264* (2013.01); *G06N 3/02* (2013.01); *G16H 40/63* (2018.01); *G16H 50/20* (2018.01); *A61B 5/167* (2013.01); *A61B 2503/12* (2013.01); *G06N 3/084* (2013.01); *G06Q 10/063112* (2013.01)

(58) Field of Classification Search
None
See application file for complete search history.

(56) References Cited

U.S. PATENT DOCUMENTS

2005/0177058 A1* 8/2005 Sobell ................ A61B 5/16
600/545

* cited by examiner

*Primary Examiner* — Daniel C Puentes

(57) ABSTRACT

This invention, which focuses on personality and aptitude matching by psychophysiologic response to stimuli, is referred to as Brain Matching. In general terms, this invention starts by selecting highly specialized skill sets and top performer group for each skill set. The various groups are analyzed though psychophysiologic stimuli testing by using basically the same testing consisting of large numbers stimuli tests in a consistent testing environment. Stimuli tests can range from hundreds to thousands of images each producing a brainwave response. Neural Networks, Artificial Intelligence, Deep Learning computers look at the test results, highly specialized group by other highly specialized group to reduce the groups signature/response commonality into a template. Test subjects are then tested using the same stimuli. The subject's test results are analyzed for correlation with the various specialized expert groups.

7 Claims, 11 Drawing Sheets

| Peak | Latency | Evoking Stimuli | Interpretation |
|---|---|---|---|
| P1 | 50 ms (auditory) | None specific | reflects level of arousal; suppression of unattended information |
| | 100 ms (visual) | | |
| N1 | 100 ms (auditory) | None specific | Selective filtering, basic stimulus characteristics, initial selection for later pattern recognition |
| | 100 ms - 165 ms (visual) | | |
| P2 | 150-275 ms (auditory) | None specific | Selective attention, Stimulus change, feature detection, short-term memory |
| | 200 ms (visual) | | |
| N2 | 200 ms (auditory) | None specific | Detects changes in stimuli that are attended to |
| | 156–189 ms aka N170 (visual) | human faces, complex objects, words | Facial and/or expert object recognition |
| | 100-300 ms Auditory & Visual | Go/NoGo | inhibition |
| MMN | 100-250 ms (auditory) | physically different infrequent stimuli among other more frequent stimuli | early pre-attentive sensory memory |
| P3 | 300 ms | Attention to stimuli, low probability of targets | memory updating, stimulus discrimination and responses preparation |
| | 300 ms | Novel stimuli, not requiring attention | involuntary attention, inhibition |
| N400 | 200–500 ms. peaks: 475 ms (auditory) 525 ms (visual) | Semantically deviant words | Semantic meaning |
| | 300-500 ms aka FN400 | memory tasks | familiarity of stimuli |
| P600 | 350-1200 ms (non-specific) | Recognition memory tasks (old/new decisions) | recollection |
| | 600ms (non-specific) | Syntactic and morphosyntactic violations | syntactic reanalysis and repair |

FIG 12

BRAIN MATCHING

CROSS-REFERENCE TO RELATED APPLICATIONS

This application claims priority from U.S. Non-Provisional patent application Ser. No. 15/530,894; titled "Brain Matching" filed Mar. 20, 2017. This application also claims priority from U.S. Provisional Application 62/310,542; titled "Brain Matching" filed on Mar. 18, 2016.

This application incorporates by reference the following U.S. patent and patent applications: U.S. Pat. No. 8,684, 926B2, US20150164363A1, and US20140163408A1.

BACKGROUND

The field of this invention relates to electronic brain monitoring techniques.

We spend a significant amount of time and money trying to determine "who am I?", "what do I want to be?" and "what am I naturally good at." One of the basic questions to a child or young adult is "What do you want to be when you grow up?" Their initial response may reflect something exciting as a fireman, policeman, or sports star. Others may take a more human approach of being a nurse, doctor, or veterinarian. Many times, the basis for their decision is on something they saw on TV, internet or heard from their peers. Others are influenced by their parents' wishes or a school teacher's guidance. This "who do I want to be?" question takes a more serious course when a young high school student starts to elect specialized courses to focus on college. A high school student's college selection decisions will have significant impact on the rest of his/her life. Once in college, the average student changes their major more than twice. People will normally be happy doing things that come easy to them. One risk is that people don't find out what they want to do until years down the road.

Employers spend a lot of time and money searching for young college graduates to train to become professionals. Yet a large number of personnel quit for something else after years of investment. A classic example is the U.S. military, who spend billions of dollars to attract skilled individuals. The military recruits for basic and advanced training and then invests significantly more money in specialized training for military gunners, drivers, pilots, computer operations, weapon specialists, etc. Finding personnel to train for highly specialized positions such as fighter pilots, special operations personnel, and specialized physicians is an especially expensive and time consuming process.

Many persons may have strong skills yet are not aware because they may not have been exposed the areas where they have strength. An example would be a young adult that never played an instrument but has an inherent ability to do well in music if exposed. The problem is how to identify hidden skills in a person that has the ability to be great in a particular profession but is not aware of this since he was never exposed to the profession.

Administration of standardized tests such as the Myers-Briggs or similar tests measuring knowledge, personality traits, or cognitive ability requires a substantial amount of time for the candidate to read or listen to questions and record responses on paper or electronic media. Such tests can be compromised by the self-reporting biases of the candidate being tested. The candidate has an opportunity to consider the question and shape a response suited to how the candidate wishes to be perceived rather than providing the strictly objective response.

Tests based on written or spoken stimuli can be limited in their ability to probe the full spectrum of the psyche of the candidate. Conventional tests can also limit the responses to stimuli to very simplistic binary answers or multiple choice answers recorded by pencil, paper, or electronic means. Interpretation of test results requires subjective assessments of skilled personnel. Consequently, conventional testing to predict the suitability of persons to perform particular functions has often not proven to be reliable due to the subjective nature of the assessment.

Conventional personality type indicators classify persons in a relative small number of specific categories. For example Myers-Briggs classifies a person in 1 of 16 categories. Thus conventional personality type indicators may not have the fidelity necessary to capture traits that are indicative of certain subgroups of the human population, such as certain high performing personnel.

DESCRIPTION OF THE SEVERAL VIEWS OF THE DRAWINGS

FIG. 12. Is a chart showing the various scientific designations for brainwaves' response to stimuli.

DRAWING REFERENCE NUMERALS

Figure 1:
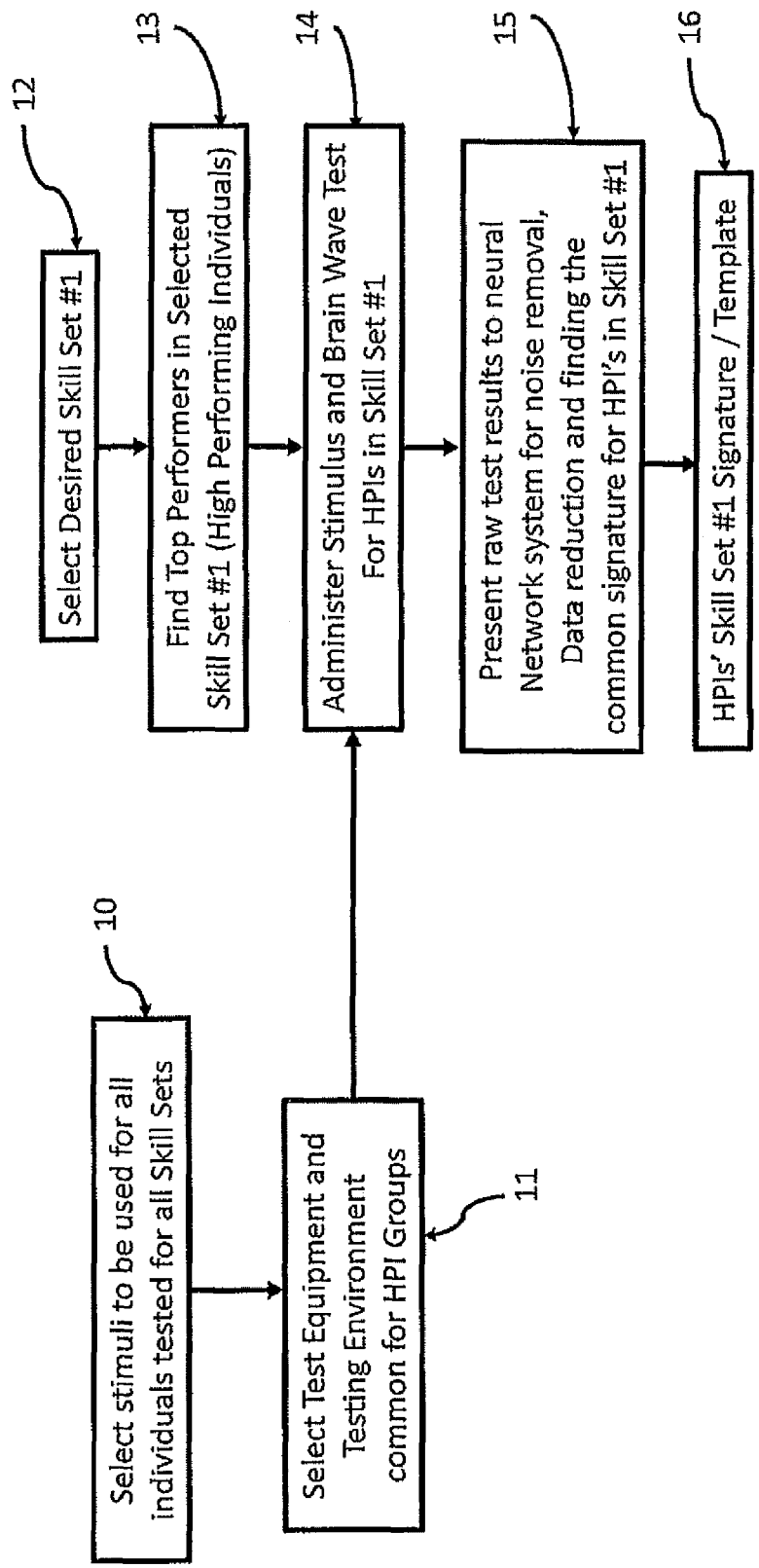
FIG. 1 illustrates a block diagram of the steps used to select the stimuli to develop the common test in conjunction with selecting one desired skill set and a group of high performing of individuals then the process utilizing neural networks to develop a signature/template.

10 Selection of Stimuli
11 Selection of Testing Equipment and Testing Environment
12 Selection of the Desired Skill Set
13 Finding High Performing Individual in the Desired Skill Set
14 Administering Stimulus and Brain Wave Test 15 Presenting raw test data to a computer Neural Network system to search for commonality and reduce noise.
16 Developing the Desired Skill Set group signature/template
21 Common Test and Environment
22 Selecting Special Skill Set #2
23 Finding High Performing Individuals in the Desired Skill Set
24 Administering Stimulus and Brain Wave Test
25 Presenting raw test data to a computer Neural Network system to search for commonality and reduce noise.
26 Developing the Desired Skill Set group signature/template
31 Common Test and Environment
32 Selecting Special Skill Set N
33 Finding High Performing Individuals in the Desired Skill Set N
34 Administering Stimulus and Brain Wave Test
35 Presenting raw test data to a computer Neural Network system to search for commonality and reduce noise.
36 Developing the Desired Skill Set group signature/template for Skill Set N
41 Common Test and Environment
42 Select Individual to be Tested
43 Administer Stimulus and Tests to Selected Individual
44 Data reduction and producing the Tested individual's brain template
45 Search/Comparison Algorithm that compares the Tested Individual's template to the Special Sill Sets HPIs templates.
46 Determine if Tested Individual matches any Special Skill Groups templates.
101 Identification of High Performing Individuals of a particular skill set
102 Identification of Common Physiological Characteristics
103 Identification of Stimuli for testing
104 Identification Physical Measures of Response to Stimuli
105 Test Stimuli on High Performing Individuals of the same skill set.
106 Determine confidence in match or no match
107 Administer Stimuli set to test subjects
108 Correlate Candidate Responses
109 Refine Stimuli Set
110 Candidate Response Match?
111 Add to Group of Interest
112 Reject
201 Group of Interest Stimuli
202 Group of Interest Signature
203 Stimuli Set Database
204 GOI Signature Database
205 Administer Stimuli Set to GOI Candidates
206 Correlate Candidate Response w/GOI Response
207 Report Correlation
301 EEG data processing computer
302 EEG sensors
302a EEG sensor cable harness
303 Interviewee
306 Interviewee support structure
308 Interviewee input device
312 Graphical display device
314 Control Computer
315 Data and Synchronization cable
316 System Support Structure
317 Stimuli Database
318 GOT Signature Database
501 EEG data processing computer
502 EEG sensor
503 Interviewee
504 EKG Sensor
505 Respiration Band
506 Chair
507 Shaker
508 Interviewee input device
509 EKG data processing computer
510 Audio output device
511 RF Transmitter/Receiver
512 Graphical display device
513 Camera
514 Control computer
515 Data synchronization
516 System Support Structure
517 Stimuli Database
518 GOI Signature Database
710 Data bus
720 Display
730 User Input
740 Fixed Storage
750 Removable media
760 I/O controller
770 Memory
780 Processor
790 Network Interface
800 Network
810 Client
820 Client
830 Remote Platform
840 Server
850 Database
860 Data store
870 Data store

DETAILED DESCRIPTION

According to an implementation of this disclosure, "Brain Matching" techniques may be employed to perform personality and aptitude matching by measuring psychophysiologic responses to stimuli. In general terms, highly specialized skill sets may be selected along with expert groups for each skill set. The various groups may be analyzed though psychophysiologic stimuli testing by using a substantially standardized test of large numbers of stimuli in a consistent testing environment. Standardized stimuli tests can include hundreds to thousands of images each of which may generally produce a brainwave response in a test subject. Machine learning techniques employing deep neural networks and/or other techniques driven by artificial intelligence may analyze the test results.

In an implementation of this disclosure, responses from test subjects in a highly specialized expert group to a standardized test stimuli may be compared using deep neural network techniques to responses from other test subjects of that expert group to identify a combined signature or other response commonality for that type of group. Response signatures or commonalities may be stored as template for that expert group. In a similar way, templates for various other specialized expert groups may be determined based on their response to the same standardized test stimuli. These templates may be compiled into a set of expert group templates New test subjects may then be tested using the standardized test stimuli. The results of the new test subjects may be analyzed for correlation with the set of expert group templates. Subjects with a strong correlation to a specific expert group template may be determined to have a significant probably of performing well in the specialized area associated with the specific expert group associated with that specific template.

Additional benefits of Brain Matching in accordance with an implementation of this disclosure, may be that a person turned away from the initial group could be guided to areas where he/she is perhaps better suited to mature professionally using the knowledge that he/she responds to stimuli in a manner similar to another specialized expert group.

Implementations of this disclosure may solve the long-standing problem of identifying candidates that are well suited to perform a particular function of interest. This can be accomplished by matching the psychophysiologic response of a candidate exposed to a set of sensible stimuli with the psychophysiologic response characteristic of a population of persons skilled at performing the function of interest exposed to the same set of sensible stimuli. In one implementation, the psychophysiologic response may be observed by sensing a variety of brainwaves resulting from graphical stimuli. The system and process is capable of also presenting stimuli using any of the five human senses and observing psychophysiologic responses such as brainwaves, pupillary response, eye movement, heart rate, heart rate variability, respiration, electrodermal activity, and other responses well known in the art.

Technical literature is replete with examples of distinctive differences in the personality traits of particular groups of professionals (e.g., surgeons, astronauts, pilots) compared to the general population. Examples include: "How Do Astronaut Candidate Profiles Differ from Aviation Airline Pilots?;" Aviation Psychology and Applied Human Factors 2011; Vol. I(I):38.44; "Personality as a Predictor of Professional Behavior in Dental School;" Journal of Dental Education; Vol. 69, No. 11; 1222; and "A Psychological Profile of Surgeons and Surgical Residents," Journal of Surgical Education; Volume 67/Number 6, 359-370.

Figure 6:
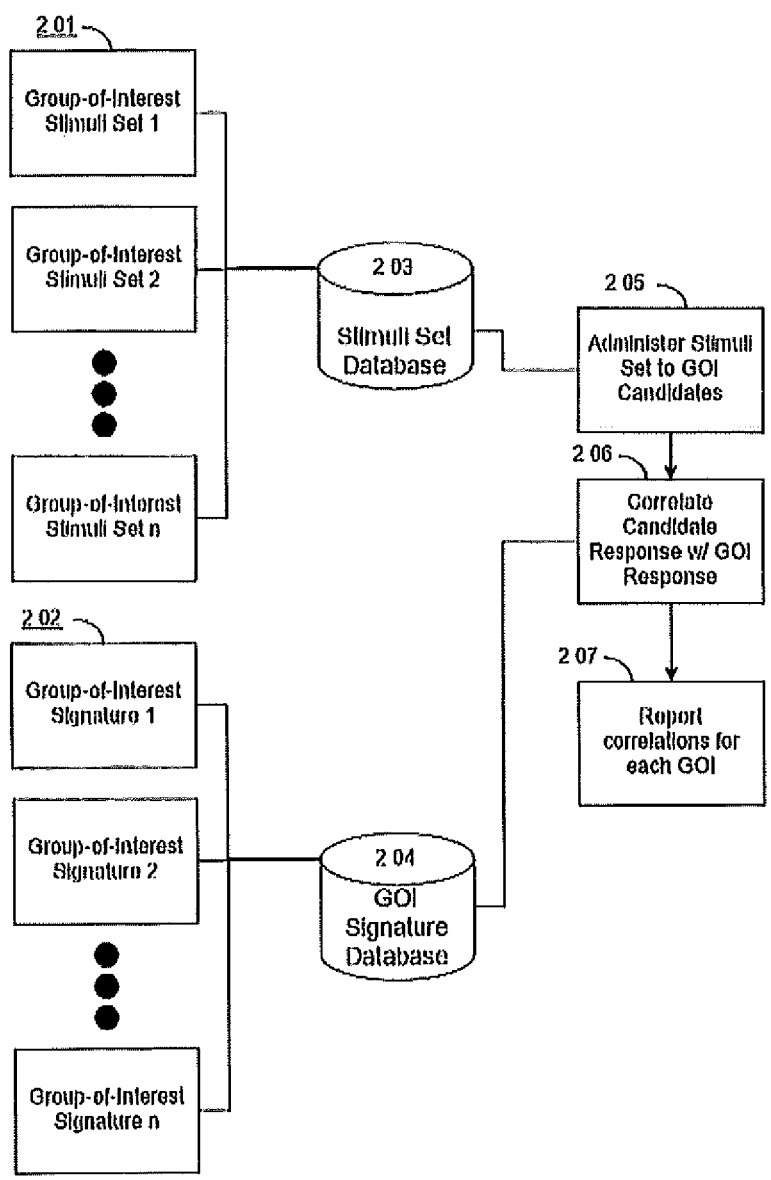
FIG. 6 illustrates a block diagram of the steps taken to assess the suitability of multiple candidates for multiple functions, according to an implementation of this disclosure.

In "The Warfighters of Today: Personality and Cognitive Characteristics of Rated Fighter Pilots in the United States Air Force," Florida State University Libraries Electronic Theses, Treatises and Dissertations, 2010, the author demonstrates that the fighter pilots as a group have distinctively different scores on the Revised NEO Personality Inventory (NEO PI-R) test compared to the general population as illustrated in FIG. 6.

Implementations of this disclosure may facilitate the assessment of suitability for a particular job or task that spans the range from an individual applying for a single position open for a particular employer to many thousands of people trying to identify which of many positions they might be suited (e.g., military occupational specialty). Implementations of this disclosure can also be used for persons to explore vocations they are suited for, so that they can pursue appropriate fields of study to prepare them for entry or transition in the work force.

One problem with any new data stream can be knowing how to make sense of it, understand the information it contains, and exploit the information for some purpose. Brainwaves can be characterized as time-varying voltages that are caused by neural activity and measured with an array of sensors in contact with the scalp. In an implementation of the disclosures, pattern matching may be employed to identify individuals whose brain responses to certain stimuli are similar to that of individuals who are very successful or talented in particular fields. As an example, if a young person's brain wave signature response to stimuli is similar to an expert aircraft pilot, then it may be expected that the young person might also, with training, become an excellent pilot.

Brain waves may include weak signals having a significant quantity of noise. Implementations of the disclosure may take an exploratory approach, that can identify correlations in brain wave data and extrapolate patterns based on machine learning techniques employing deep neural networks and/or other artificial intelligence techniques.

In implementations of this disclosure machine learning techniques may be based on statistical classification or computational neural nets (inspired by but not to be confused with biological neural nets such as the human brain). These machine learning techniques can enable the use of many different inputs without regard to a user's ignorance as to which inputs are important or even having a concept of what the inputs represent. In the case of a neural network such as a multi-layer perceptron, a large number of inputs can be used including those used to characterize the stimuli, the brain waves of the person being measured, and temporal delays used to model the brain's latency. As the network operates, weights on processing nodes may be adjusted nonlinearly using algorithmic feedback known as back-propagation. Over time and many empirical examples in a training data set, the input nodes that are unimportant to pattern classification can have their weights adjusted towards zero while those that are significant can have weights that increase. In this way, the neural network can "learn" (through weight adjustment) different patterns such as the brain wave patterns of exemplar humans who represent the best, most successful, and most talented individuals in particular domains (or as described above, expert groups). These different patterns can be expressed as a vector of the outputs of the neural network, but they can be quite recognizable and characteristic of the various exemplar humans. Thus, after training, the neural network can now classify new persons as having brains that respond most similarly to one of the exemplars (or expert group template as discussed above). One obvious use for such a neural network may be to identify good fields of endeavor to suggest to young people. If a young person's brain wave response to certain stimuli is similar to an exemplar individual in a particular field, then it may be likely that the young person's brain is predisposed enable success in that field.

A statistical classifier can be equivalent to a computational neural net for pattern recognition. Thus, implementations of this disclosure may employ techniques in addition to neural networks, such as similar machine learning methods, or other artificial intelligence driven techniques.

The inputs to the machine learning techniques discussed herein can include the brain waves of a test subject who is responding to certain stimuli. Brain waves can vary by frequency and amplitude as well as the rates of change in frequency and amplitude based on changes in stimuli. Furthermore, in addition to brain waves, other types of psychophysiologic responses may be analyzed including but not limited to pupillary response, eye movement, heart rate, heart rate variability, respiration, and electrodermal activity. All of these factors can be inputs to the machine learning system because they are potentially correlated to brain response. For example, brain wave frequency can be correlated to state-of-mind, computational load on the brain, and certain personality characteristics such as the degree of extroversion/introversion.

A computing device may execute various procedures for determining a brainwave signature or template for an expert group of high performing individuals, according to implementations of this disclosure. For example, FIG. 1 shows an example procedure, where at 10 stimuli may be selected to be used as standardized stimuli for all individuals tested for all skill sets. This test may consist of a significant number of stimuli such as hundreds or thousands photos of various subjects, numbers, letters, objects, faces, abstract art, geometrical shapes, or 3-D presentations. An average human brain can process 12 frames or pictures a second. At this speed, it is hard to recognize photos consciously but the human brain functions subconsciously at a faster rate and generates measurable brain response activity to various stimuli. With the brain processing 100 to 500+ photos a minute, thousands of diverse photos can be used. Photos may be selected that have a bold subject and solicit a strong response.

In implementations of this disclosure, once the standardized stimuli selection has been made, the common test equipment and testing environment 11 can be selected. Since a test goal may be to measure variations between individuals, the test setup may be configured to reduce as many variables as possible.

As discussed above, one benefit of implementations of this disclosure may be to determine if unknown persons are mentally wired like high performing individuals. The first step may be to select the sought after skill set at 12 and then identify the high performing individuals in this area at 13. For example, a first set of subjects may be a set of high performing individuals with respect to a sought after skill and the first selection criteria may be the sought after skill determined at 12. In some implementations a second set of subjects may be a randomly sampled set of persons selected from the general population or a related baseline set of test subjects. The second selection criteria may be that the second set of subjects are randomly selected or otherwise selected in a manner that results in a suitable baseline of personnel.

Once test subjects are identified, they may be presented with the standard stimuli at 14. For example, a sensory presentation device, such as a video screen or projection system may be communicatively connected to a computing device. The sensory presentation device may present the first sequence of stimuli from the standardized stimuli to the set of high performing individuals. In some implementations, the sensory presentation device may also present the first sequence of stimuli to the second set of subjects.

During or after presentation of the standardized stimuli, one or more electrodes operatively connected to each of the high performing individuals and in communication with the computing device may detect a first set of one or more voltage fluctuation sequences from each of the high performing individuals. In some implementations, during or after presentation of the standardized stimuli, one or more electrodes operatively connected to each of the second set of subjects and in communication with the computing device may detect a second set of one or more voltage fluctuation sequences from each of the second set of subjects.

Once the high performing individuals complete the test or as they complete the test, their raw test data can be submitted at 15 to a computing device implementing machine learning techniques that can look for commonality in brainwave data among the subjects of the expert group. For example, a neural network executing on the first computing device may determine a pattern of voltage fluctuations that are characteristic of the first set of voltage fluctuations. This characteristic pattern may be stored as a template and associated with the high performing individuals at 16. In some implementations, the neural network may determine a pattern of voltage fluctuations that are characteristic of the first set of voltage fluctuation sequences and not characteristic of the second set of voltage fluctuation sequences. This determined pattern that is not characteristic of the second set of voltage fluctuation sequences may be selected as the characteristic pattern for the high performing individuals and stored as a template.

In some implementations, machine learning techniques such as neural networks may execute on computing devices such as one or more remote servers executing in a cloud computing environment in communication with a local computing device and/or sensory presentation device as discussed herein.

In some implementations, the procedure discussed with respect to FIG. 1 may include providing, by the first computing device, a recommendation for a selection of subjects from among a third set of subjects based on the pattern of voltage fluctuations. For example, a third set of subjects may be presented with the standardized stimuli and their brainwave responses to the stimuli may be compared to the stored template associated with the high performing individuals. The brainwave responses of a subset of subjects within the third set of subjects may be determined to exhibit a correlation with the template that exceeds a threshold value. In response to this determination, this subset of the third set of subjects may be recommended for consideration for performing the sough after skill associated with the high performing individuals. In some implementations, recommendations as discussed herein may be provided to other systems such as employee recruitment systems or components of enterprise human resources information systems and serve as a basis for further functionality of those systems. In some implementations, recommendations may be provided to an interface for a user of a computing device.

Figure 2:
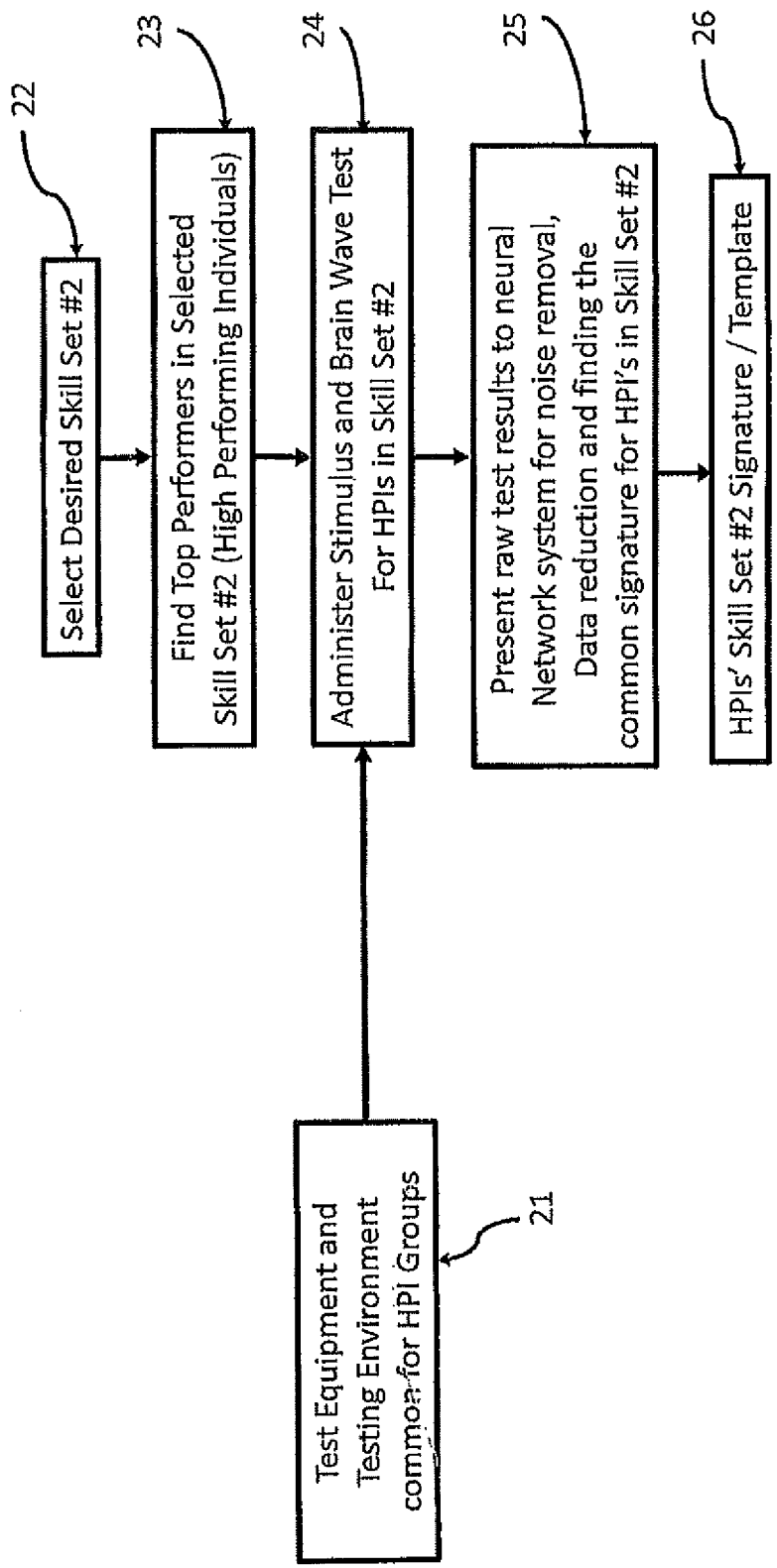
FIG. 2 illustrates a block diagram of the steps taken to repeat part of the process shown in FIG. 1 selecting a second skill set but utilizing the same tests and environments.

FIG. 2 shows a similar process for identifying a new skill set, 22 then selecting the top performers with that skill set, 23. The same stimuli test and conditions, 21 may be administered, 24 to assist in identifying a test subject with a better fit into another desired skill area. Similarly, to FIG. 1 neural network processing, 25 may be performed on the group of experts' raw test data to determine a template or signature of the group. A signature or template could be made by looking at a number of skill experts in the desired skill set area since the test data results are very large datafiles and can be at the giga- or terabyte levels. Neural networks are designed for large data and high number of comparisons. At least 10 high-performing individuals should be used to develop a template. Hundreds of HPIs would be statically better if possible for developing a template or signature.

Figure 3:
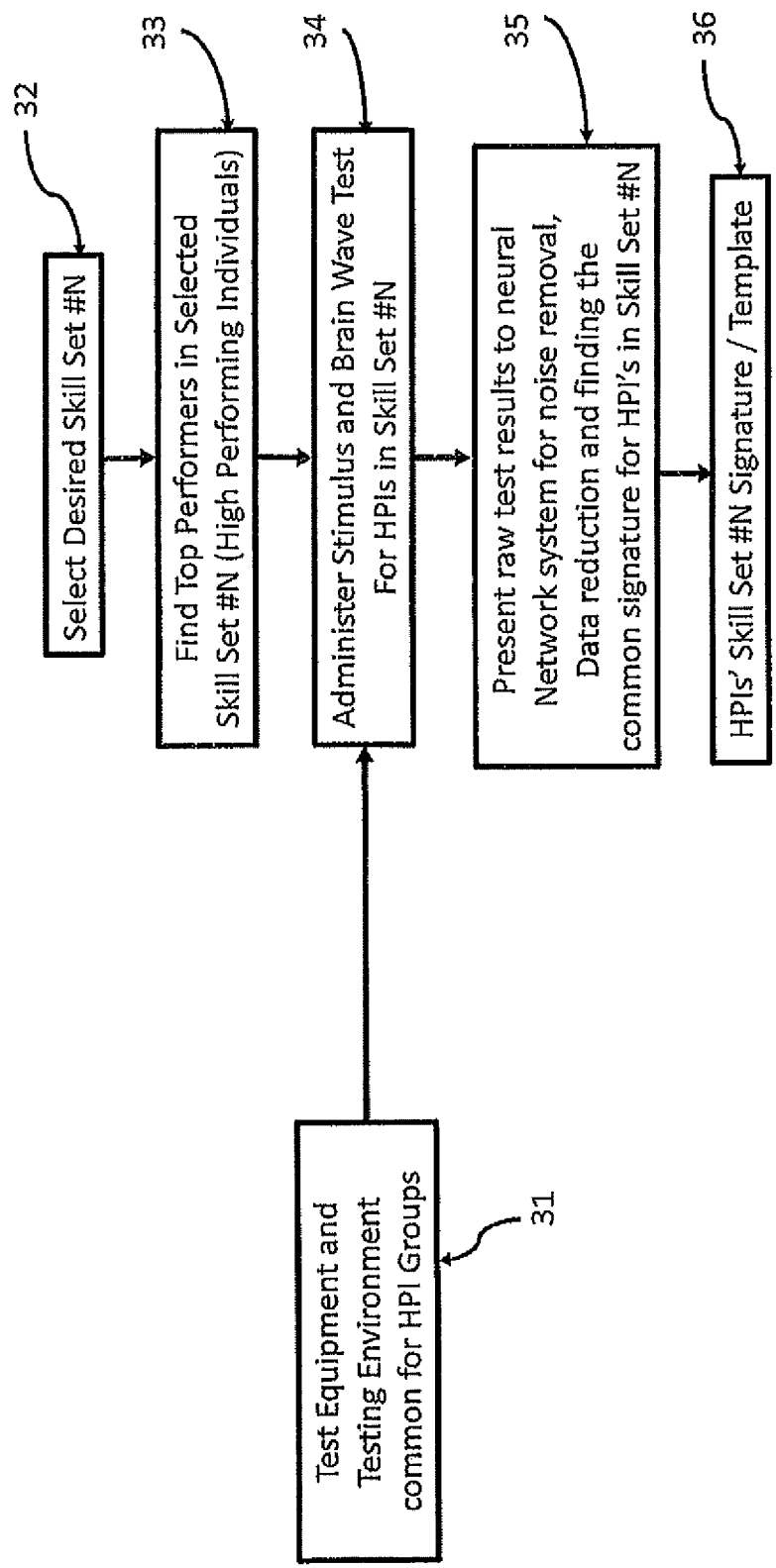
FIG. 3 illustrates a block diagram of the steps taken to repeat the process in FIG. 2 but this is repeated N times.
Figure 4:
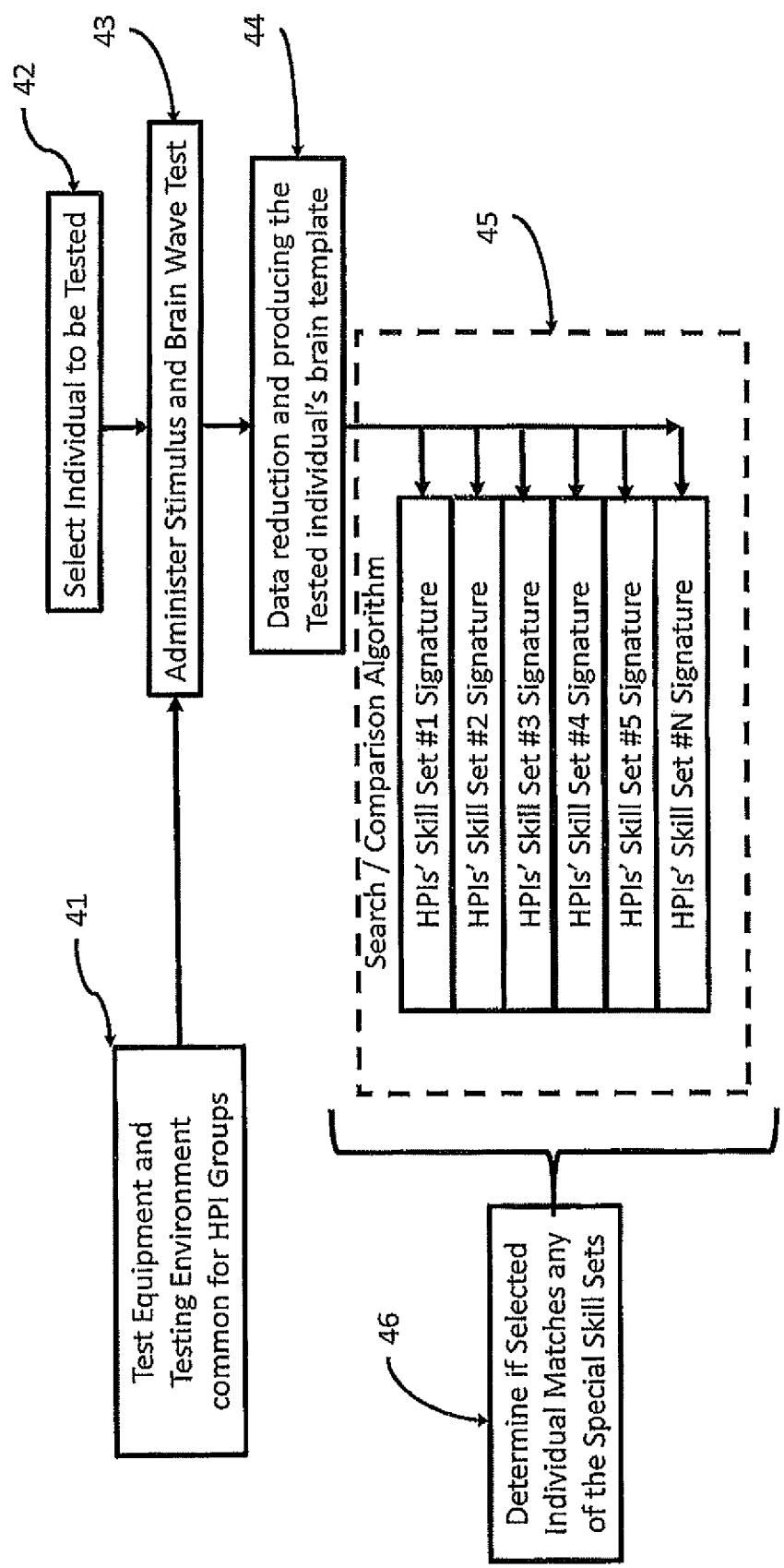
FIG. 4 illustrates a block diagram selecting individuals to be tested, tested, compared to special skill set groups and determining any relationship of the tested individual to any of the special skill groups.

FIG. 3 expands FIG. 2 with basically the same process but selecting N desired skill sets, 32. The more desired skill sets and high performing individuals tested, the better the signature/template can be derived. FIG. 4 focuses on the unknown individual, 42 to take the standard test to determine if he has a strong match to any of the high performing individuals group signatures, 46. The process is similar to FIG. 3 but instead of testing high performing individuals, the testing may be administered to unknown skill set persons. The goal is to see if the unknown person is a fit to one of the desired skill set group.

Figure 5:
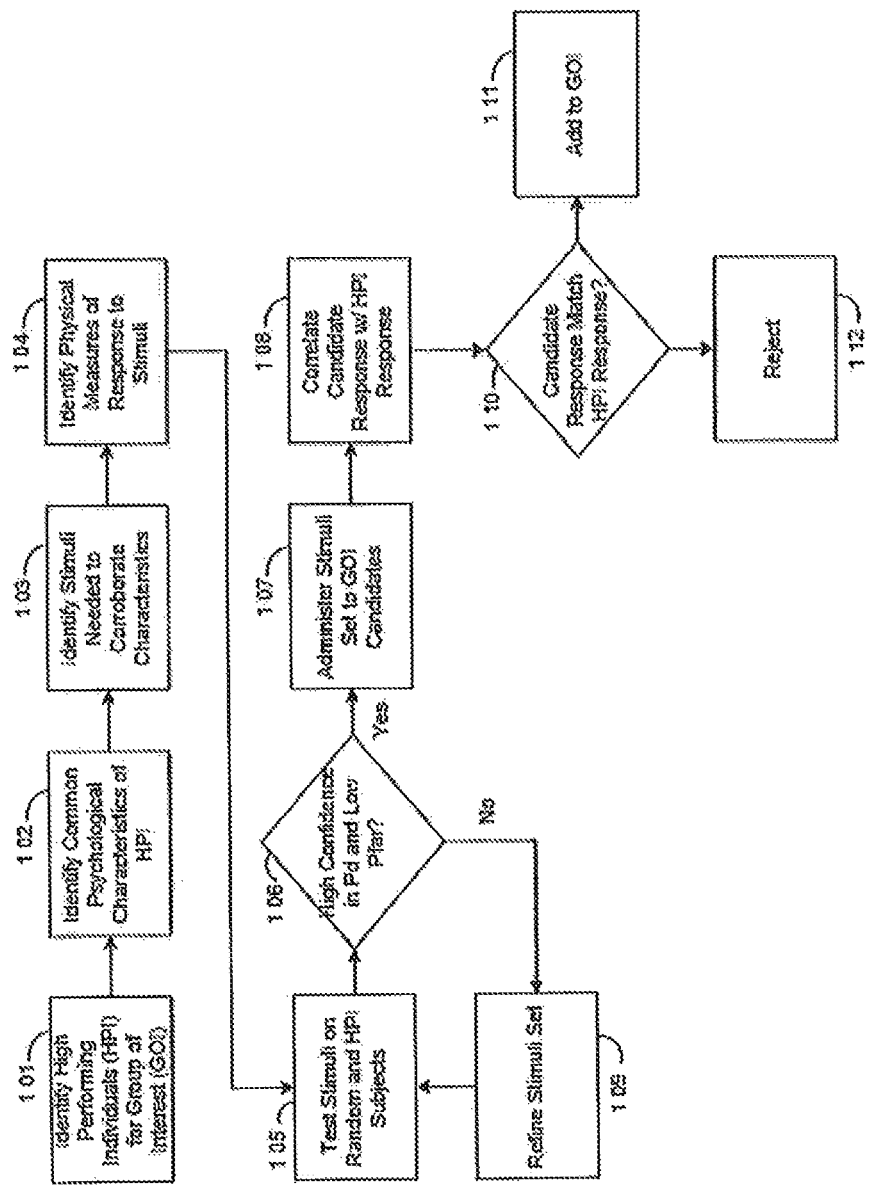
FIG. 5 illustrates a block diagram of the steps taken to assess the suitability of multiple candidates for a single function, according to an implementation of this disclosure.

In FIG. 5, several steps are illustrated that enable the objective prediction of suitability of a candidate to a particular task or organizational function. The first step, 1 01, of the process may identify the high performing individuals (HPI) in a group of interest (GOI) that performs a particular task or organizational function. In step 1 02, the HPI can be evaluated to identify the common psychological characteristics or traits which are distinctive to the HPI of the GOI.

In step 1 03, psychological stimuli may be identified which will result in physiologic responses which can be observed by the sensors of the system, 1 04. These stimuli could be any of those that affect the five human senses; sight, hearing, touch, taste, smell. Stimuli of step 1 03 and the physical measures of step 1 04 may be evaluated as effective predictive indicators of suitability for a particular task or function by testing people from the general population and HPI. The psychophysiologic response of the HPI to the stimuli set is compared to that of the general population in step 1 06.

An example of how stimuli elicit psychophysiologic responses which are indicative of personality traits is an electronic administration of something like the Big Five Personality Test, which poses several statements to a test subject and asks the test subject to indicate how strongly the statement accurately portrays reflects the test subject. For instance, the test may state that the test subject tends to find fault with others. The test subject responds by filling coloring one of five circles that represent degrees of agreement from "Strongly Disagree" to Strongly Agree." Asking a test subject the same questions via text, visual representation or speech and monitoring the brainwave response by EEG sensors. The N-400 brainwaves may be event-driven psychophysiologic responses triggered by external stimuli that challenge the test subject with agreement or disagreement with self-concept of the test subject. When instructed to assess how well statements describe the test subject, the amplitude of the N-400 may be proportional to the degree of agreement with the statement without the test subject having to indicate their answer by coloring bubbles on a paper form.

FIG. 12 is a Table listing several brainwave responses to various stimuli. For instance, the P-300 brainwave has proven very effective at indicating a test subject's level of recognition of sounds, words, numbers or images. Appropriate stimuli can be generated and presented to the test subject and responses recorded. Because the purpose of this system is to establish characteristic patterns of response to stimuli, the exact stimuli need not be limited to elucidating personality traits alone.

In all cases, the response to stimuli may result in a set of measured values with fixed and known ranges. One example is measured voltage from a brain wave as measured by an electrode placed at a particular location on the scalp. To classify a response, a set of these measured values in addition to a digital description of the particular stimuli can be input into a classifier such as a neural net (e.g., a multi-layer perceptron using back-propagation during training) or equivalent other classifier algorithm. The output may be a vector of values that characterize a group such as individuals who perform well, are experts in, or are talented in a particular field. This vector of outputs may be a refined version of the raw values measured and thus a good, general method of measuring the response to stimuli. The classifier described in this paragraph is a common component in all embodiments.

If the response of the HPI is distinctly different from that of the general population (e.g., their signature) so that the HPI are identified to be a HPI of the GOI with a high degree of probability (Pd) and low false alarm rate (Pfar), then the set of stimuli may be validated to be reliably predictive and can be administered to candidates. If not, then the stimuli set may be modified in step 1 09 and re-evaluated in steps 1 05 and 1 06 until the stimuli set is deemed sufficiently predictive.

Once the stimuli set is validated as predictive with high Pd and low Pfar, it can be administered to candidates for the GOI in step 1 07. The psychophysiologic response of candidates to the stimuli set may be correlated to that of the HPI response to the same stimuli set. The strength of the correlation predicts how well the candidate matches the response of the HPI and thus probability that the candidate will also be a strong performer in the GOT; step 1 10. If the strength of match exceeds a threshold value, the candidate may be deemed to be a fit in the GOI, step 1 11. If not, the candidate i may be deemed unlikely to fit in the GOI.

FIG. 6 illustrates an extension of the process and system of described in FIG. 5. The process in FIG. 2 evaluates the degree of fit of candidates to multiple groups of interest (GOIs). The steps of FIG. 5 may be implemented for multiple tasks or functions so that a library of diagnostic stimuli sets 2 01 is populated in database 2 03. The distinctive signatures for HPI of each task 2 02 may populate a signature database, 2 04. The library of stimuli data sets may be administered to candidates for the corresponding GOIs in step 2 05. The response of the candidate to the stimuli may be correlated to those of the signatures characteristic of the HP's of the GOIs in step 2 06. Closeness of fit of the candidate to the GOIs represented may be tabulated in a report 2 07.

Figure 7:
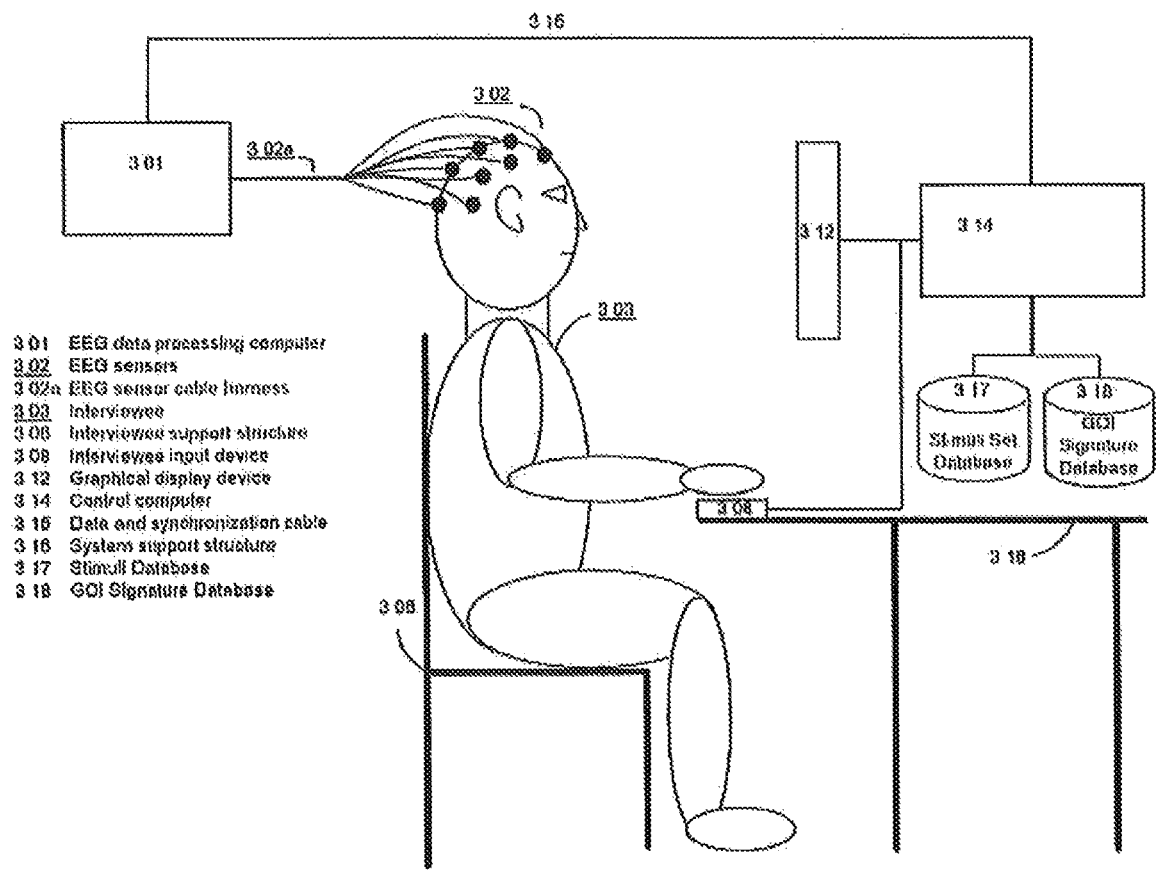
FIG. 7 illustrates instrumentation employed is the essential embodiment of the system working on brainwave psychophysiologic response to external stimuli, according to an implementation of this disclosure.
Figure 8:
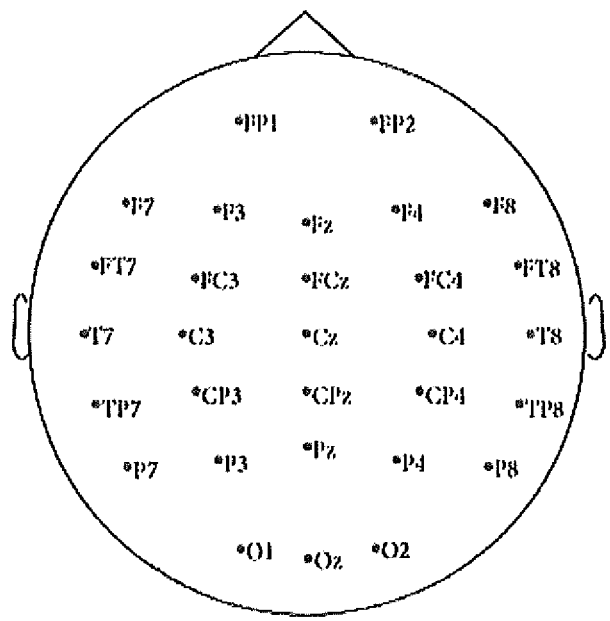
FIG. 8 illustrates brainwave sensor locations for 30 sensors, according to an implementation of this disclosure.

FIG. 7 illustrates an embodiment of this invention. An interviewee 3 03 is seated before a graphical display device, 3 12. In this particular embodiment, stimuli 3 17 may be graphical in nature and are displayed on the graphical display device, 3 12. Stimuli elements, for instance still images, may be displayed at fixed intervals for fixed durations of time in the method of rapid serial visual presentation (RSVP) which is well known in the art. Graphical presentation of stimuli by RSVP typically displays images at a rate of 5 to 10 images per second.

One or more sensors 3 02 may be arranged on the test subject's head in locations according to locations illustrated in FIG. 4 for a 30 channel system, in an embodiment. The number and location of channels may differ upon the stimulus presented to the interviewee 3 03. The sensors and data collection and processing collectively facilitate electroencephalography (EEG). Sensor locations may be selected to obtain strong signals for specific brainwaves resulting from the RSVP stimuli. Brainwave signals may have characteristic shape, polarity and latency which is well established in the art. FIG. 12 Table presents well known brainwave signals, their polarity, latency, evoking stimuli and interpretation.

Communication means 3 15 may provide a channel for data to be transferred between EEG data processing computer 3 01 and control computer 3 14. Channel 3 15 may also provide the timing data needed for EEG data processing computer to know when stimuli is presented to the interviewee 3 03 so that brainwave latency can be computed. This channel may be a wired or wireless connection, and may use any data format or protocol known in the art.

Interviewee input device 3 08 may be used to keep the interviewee 3 03 attentive to the graphical display device 3 12 while RSVP of the stimulus data is in progress. For instance, the interviewee may be asked to indicate the display of a particular image by pressing on a keyboard or activating a switch. Input device 3 08 may also be used to measure interviewee response time, motion inhibition response and similar psychophysiologic responses.

Figure 9:
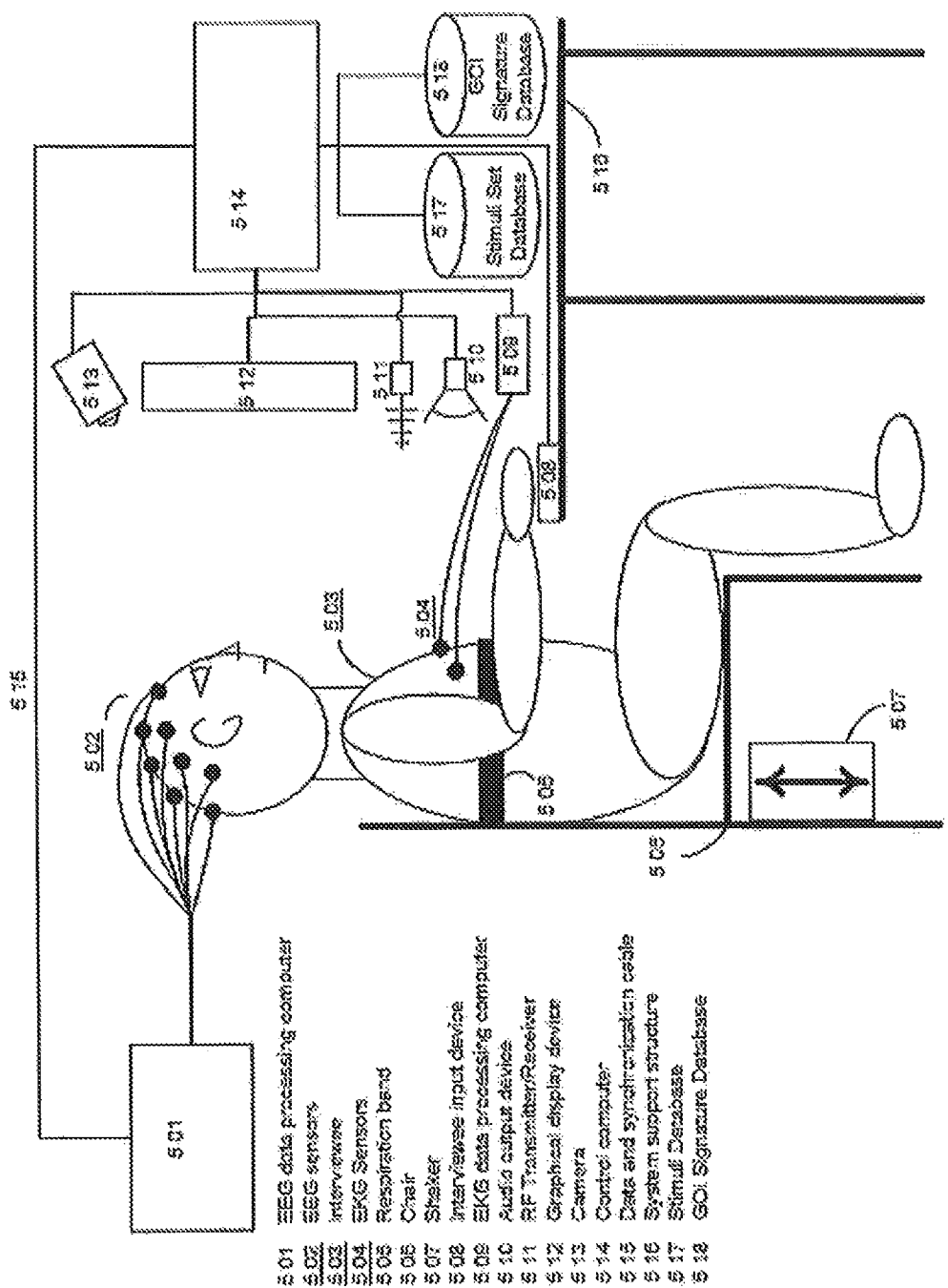
FIG. 9 illustrates instrumentation employed to produce multiple sensor inputs and multiple sensors used to observe psychophysiologic response to external stimuli, according to an implementation of this disclosure.
Figure 10:
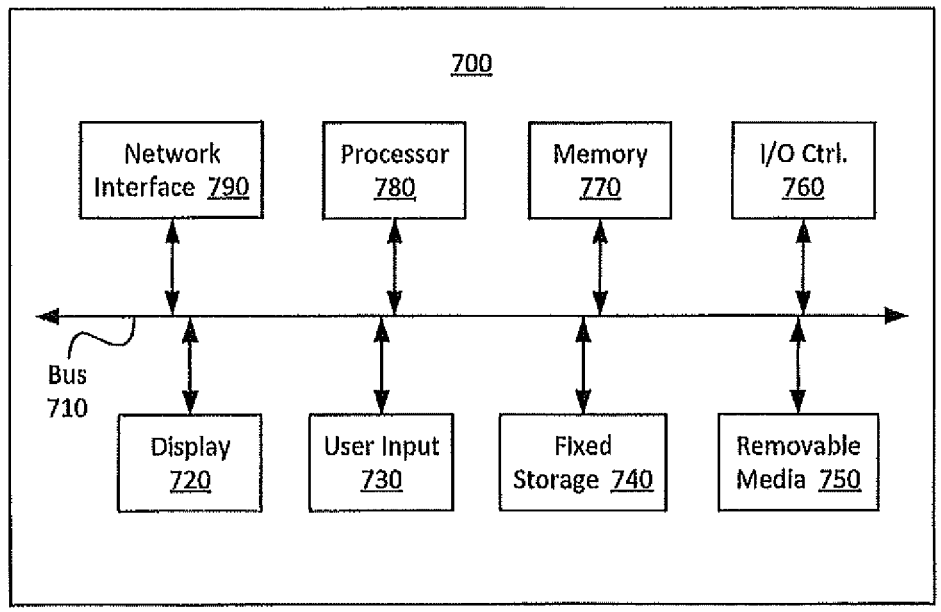
FIG. 10 shows an example computing device according to an implementation of this disclosure.

FIG. 9 illustrates a system in which stimuli may be delivered to multiple human senses and multiple sensor types are employed to observe psychophysiologic response to the multi-modal stimulation. Stimulus generating components may include the audio output device 5 10 and shaker 5 07 which is capable of imparting signals affecting the sense of touch of the interviewee. For clarity in the figure stimulus generators affecting the senses of taste and smell are not shown but could form a part of this system.

Sensors of the system described in FIG. 9 may include the EEG system components 5 01 and 5 02; electrocardiogram (EKG) sensors 5 04 and EKG data processing computer 5 09; respiration band 5 05, RF transmitter/receiver 5 10, which can be used to measure heart rate, heart rate variability and respiration using RF Doppler vibrometry and electrodermal activity; and a camera to observe pupillary response, eye movement and muscle tension. In alternative embodiments, different subsets of these sensors may be used.

The system configured in this way can produce one or more sensible stimuli and monitor one or more psychophysiologic responses to the stimuli.

Description of a Preferred Embodiment; RSVP/EEG for Single GOI

In a preferred embodiment of the invention, the process of FIG. 5 and the instrumentation of FIG. 7 may be employed to assess the fit of candidates for a single GOI.

Operation of Preferred Embodiment

In an embodiment of the invention, the process of FIG. 5 may be employed to establish the characteristic signature response of a subset of a particular group of interest that is assessed to be high performing individuals of that group of interest. Through iteration of testing and refinement, a set of graphical stimuli may be validated to distinguish between known members of the group of interest and known non-members of the group of interest with a high probability of detection and low false alarm rate. The validated stimuli set can then be administered to individuals by RSVP and resulting psychophysiologic response observed by EEG as illustrated in FIG. 7 to determine if they fit the characteristic of the GOI or not. The elements of the stimuli set may be reordered within a stimuli set presentation or mixed amongst the various stimuli sets presented.

Embodiment 2; Single Non-RSVP Input, EEG Sensors and Single GOI

In an alternative embodiment of the invention, the process of FIG. 5 and the instrumentation of FIG. 7 may be employed to assess the fit of candidates for a single GOI using stimuli sets evoking psychophysiologic response by inputs affecting senses other than the sense of vision.

Operation of Embodiment 2

In this embodiment of the invention, the process of FIG. 5 may be employed to establish the characteristic signature response of a subset of a particular group of interest that is assessed to be high performing individuals of that group of interest. Through iteration of testing and refinement, a set of graphical stimuli may be validated to distinguish between known members of the group of interest and known non-members of the group of interest with a high probability of detection and low false alarm rate. The validated stimuli set may be composed of inputs to a single human sense other than by sight such as hearing, touch, taste or smell and is administered to individuals by RSXP where X can be Hearing (H), touch (T), smell (S) or taste (T). The resulting psychophysiologic response may be observed by EEG as illustrated in FIG. 7 to determine if they fit the characteristic of the GOI or not. The elements of the stimuli set may be reordered within a stimuli set presentation or mixed amongst the various stimuli sets presented.

Embodiment 3; RSVP/EEG for Multiple GOT

An alternative embodiment of the invention may be configured to assess the fit of one or more candidates to more than one GOT by RSVP and EEG.

Operation of Embodiment 3

In this configuration of the invention, the process of FIG. 5 may be employed to establish the characteristic signature response of HPI for each of more than one GOIs. For each of more than one GOIs, a set of graphical stimuli may be validated to distinguish between known members of each GOT and known non-members of each GOI with a high probability of detection and low false alarm rate. The multiple stimuli sets associated with each GOI can then be administered to individuals by RSVP and resulting psychophysiologic response observed by EEG as illustrated in FIG. 7 to determine how well they fit each of the GOIs. The elements of the stimuli set may be reordered within a stimuli set presentation or mixed amongst the various stimuli sets presented.

Embodiment 4; RSXP/EEG for Multiple GOI

An alternative embodiment of the invention may be configured to assess the fit of one or more candidates to more than one GOI by RSXP and EEG.

Operation of Embodiment 4

In this configuration of the invention, the process of FIG. 5 may be employed to establish the characteristic signature response of HPI for each of more than one GOIs. For each of more than one GOIs, a set of graphical stimuli may be validated to distinguish between known members of each GOI and known non-members of each GOT with a high probability of detection and low false alarm rate. The multiple stimuli sets associated with each GOI can then be administered to individuals by RSXP and resulting psychophysiologic response observed by EEG as illustrated in FIG. 7 to determine how well they fit each of the GOIs. The elements of the stimuli set may be reordered within a stimuli set presentation or mixed amongst the various stimuli sets presented.

Embodiment 5; RSVP, None EEG Sensors, Single GOI

An alternative embodiment of the invention, a stimulus set to characterize a single GOI may employ RSVP and observations of psychophysiologic responses other than brainwaves.

Operation of Embodiment 5

In this embodiment of the invention, the process of FIG. 5 may be employed to establish the characteristic signature response of a subset of a particular group of interest that is assessed to be high performing individuals of a particular group of interest. Through iteration of testing and refinement, a set of graphical stimuli may be validated to distinguish between known members of the group of interest and known non-members of the group of interest with a high probability of detection and low false alarm rate. The validated stimuli set can then be administered to individuals by RSVP. The resulting psychophysiologic response may be observed by instruments other than EEG sensors. Candidate sensors may include one or more cameras sensitive to the visible and non-visible components of the spectrum (e.g., infrared) to monitor pupillary response, eye movement, vasodilation, muscle tension, etc.; electrocardiogram for heart rate and heart rate variability; respiration band for respiration rate and abnormalities; RF Doppler vibrometry to observe heart rate, heart rate variability, respiration and muscle movements; skin resistivity measures electrodermal activity. Laser Doppler vibrometry performs the same function as RF Doppler Vibrometry. There are many other sensor modes for observing psychophysiologic responses that are well known in the field of polygraphy that could also be employed measurements commonly used in this embodiment.

Embodiment 6; RSVP, None EEG Sensors, Multiple GOIs

An alternative embodiment of the invention, a stimulus set to characterize multiple GOIs employs RSVP and observations of psychophysiologic responses other than brainwaves.

Embodiment 7; RSXP, None EEG Sensors, Single GOI

An alternative embodiment of the invention, a stimulus set to characterize a single GOI employs RSXP and observations of psychophysiologic responses other than brainwaves.

Embodiment 8; RSXP, None EEG Sensors, Multiple GOIs

An alternative embodiment of the invention, a stimulus set to characterize multiple GOIs employs RSXP and observations of psychophysiologic responses other than brainwaves.

Embodiment 9; RSVP and RSXP, EEG Sensors, Single GOT

An alternative embodiment of the invention, a stimulus set to characterize a single GOI which may employ a combination of RSVP and RSXP in conjunction with and brainwave observations accomplished by EEG instrumentation.

Embodiment 10; RSVP and RSXP, EEG Sensors, Multiple GOI

An alternative embodiment of the invention, a stimulus set to characterize multiple GOIs which may employ a combination of RSVP and RSXP in conjunction with and brainwave observations accomplished by EEG instrumentation.

Embodiment 11; RSVP and RSXP, EEG and Non-EEG Sensors, Single GOI

An alternative embodiment of the invention, a stimulus set to characterize a single GOI which may employ a combination of RSVP and RSXP in conjunction with EEG and non-EEG observations.

Embodiment 12; RSVP and RSXP, EEG and Non-EEG Sensors, Multiple GOIs

An alternative embodiment of the invention, a stimulus set to characterize multiple GOIs which may employ a combination of RSVP and RSXP in conjunction with EEG and non-EEG observations.

Embodiment 13; Multiple Candidates Evaluated Concurrently for Each of the Embodiments Above Embodiment 14

An example or embodiment for using the Brain Matching invention may be for military service selection. Before a new recruit makes a decision on branch of service or which occupational specialty the recruit wish to pursue (Infantry, Armor, Logistics, mechanic, etc.), the soldier could be told that he is mentally wired like high performers of one or more special skill sets. The soldier would then have significantly important information to assist him and the military in investing in costly training in an area that does not come easy or enjoyable to him.

Embodiment 15

The brainwave signatures can be kept on file when a soldier enters the military. Sometimes soldiers face tremendous mental stress resulting in Post-Traumatic Stress Disorder (PTSD). The soldier that exhibits PTSD could be retested and compared to his original brainwave reading to see the degree stimuli responses have changes, possibly indicating the severity of the PTSD syndrome.

An alternative embodiment of the invention, multiple candidates may be evaluated simultaneously or asynchronously from during a fixed interval of time. Each candidate may be subjected to the same stimulus sets which may be presented in the same or different order.

Embodiment 14; Dynamic Selection of Stimuli Sets

Candidates can be evaluated by dynamically selected stimuli sets which are automatically selected by the system based on how well a candidate matches GOIs at high levels of abstraction. For instance, if a candidate's responses match better with a GOI for general engineering compared to other vocational types, the system may select stimuli sets from a lower tier of engineering disciplines that provide more specificity in engineering such as mechanical, electrical or software. Levels of specificity for any particular functional category may not be limited.

Embodiment 15; Unlimited Personally Type Indicators

Over tithe as the Brain Matching invention builds numerous GOI, these groups can be assembled to allow a test subject to identify which GOI he/she would result in the best correlation. This embodiment could assemble thousands of GOI to provide very specific matching.

Embodiment 16; Synthetic GOIs

This embodiment could allow taking the stimuli results from test subjects and group the test subjects in groups that currently have not been identified. An example is testing numerous candidate personnel who, after testing, do not fit in any GOI. Based on stimuli test results, these subjects may be grouped/pared by stimuli to form their own GOIs. Each GOI could be then examined to see which common skills, interests, and abilities they master.

Figure 11:
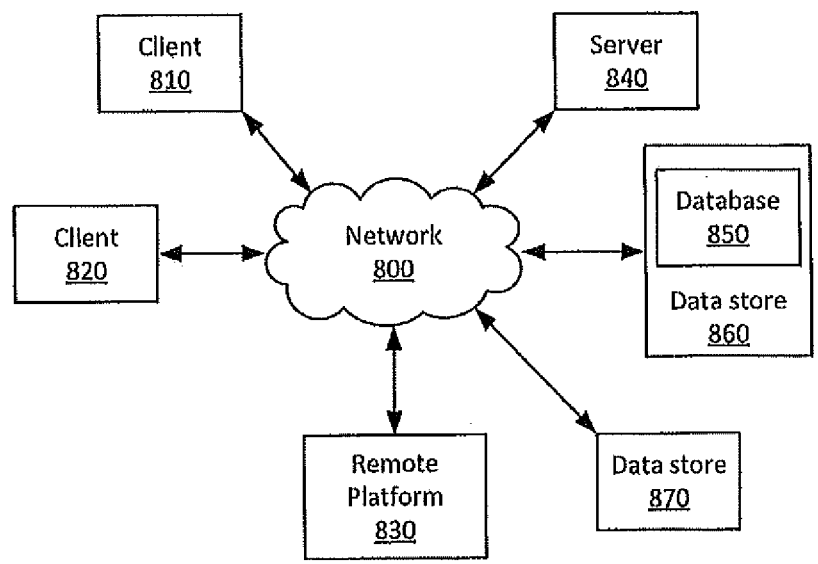
FIG. 11 shows an example network arrangement according to an implementation of this disclosure.

Implementations of the present disclosure may be implemented in and used with a variety of component and network architectures. FIG. 11 is an example computing device 700, such as a computer, suitable for implementations of the present disclosure. The computing device 700 may include a bus 710 which interconnects major components of the computing device 700, such as a central processor 780; a memory 770 (typically RAM, but which may also include ROM, flash RAM, or the like); an input/output controller 760; a user display 720, such as a display screen via a display adapter; a user input interface 730, which may include one or more controllers and associated user input devices such as a keyboard, mouse, and the like, and may be closely coupled to the I/O controller 760; fixed storage 740, such as a hard drive, flash storage, Fibre Channel network, SAN device, SCSI device, and the like; and a removable media component 750 operative to control and receive an optical disk, flash drive, and the like.

The bus 710 may allow data communication between the central processor 780 and the memory 770, which may include read-only memory (ROM) or flash memory (neither shown), and random access memory (RAM) (not shown), as previously noted. The RAM may generally be the main memory into which the operating system and application programs are loaded. The ROM or flash memory can contain, among other code, the Basic Input-Output system (BIOS) which controls basic hardware operation such as the interaction with peripheral components. Applications resident with the computing device 700 may generally be stored on and accessed via a computing device readable medium, such as a hard disk drive (e.g., fixed storage 740), an optical drive, floppy disk, or other storage medium.

The fixed storage 730 may be integral with the computing device 700 or may be separate and accessed through other interfaces. A network interface 790 may provide a direct connection to a remote server via a telephone link, to the Internet via an internet service provider (ISP), or a direct connection to a remote server via a direct network link to the Internet via a POP (point of presence) or other technique. The network interface 790 may provide such connection using wireless techniques, including digital cellular telephone connection, Cellular Digital Packet Data (CDPD) connection, digital satellite data connection or the like. For example, the network interface 790 may allow the computing device to communicate with other computing devices via one or more local, wide-area, or other networks, as shown in FIG. 12.

Many other devices or components (not shown) may be connected in a similar manner (e.g., document scanners, digital cameras and so on). Conversely, all of the components shown in FIG. 11 need not be present to practice the present disclosure. The components can be interconnected in different ways from that shown. The operation of a computing device such as that shown in FIG. 11 is readily known in the art and is not discussed in detail in this application. Code to implement the present disclosure can be stored in computing device-readable storage media such as one or more of the memory 770, fixed storage 740, removable media 750, or on a remote storage location.

FIG. 12 shows an example network arrangement according to an implementation of the disclosure. One or more clients 810, 820, such as local computing devices, smart phones, tablet computing devices, and the like may connect to other devices via one or more networks 800. The network may be a local network, wide-area network, the Internet, or any other suitable communication network or networks, and may be implemented on any suitable platform including wired and/or wireless networks. The clients may communicate with one or more servers 840 and/or databases 850. The devices may be directly accessible by the clients 810, 820, or one or more other devices may provide intermediary access such as where a server 840 provides access to resources stored in a database 850. The clients 810, 820 also may access remote platforms 830 or services provided by remote platforms 830 such as cloud computing arrangements and services. The remote platform 830 may include one or more servers 840 and/or databases 850.

More generally, various implementations of the presently disclosure may include or be implemented in the form of computing device-implemented processes and apparatuses for practicing those processes. Implementations also may be implemented in the form of a computing device program product having computing device program code containing instructions implemented in non-transitory and/or tangible media, such as floppy diskettes, CD-ROMs, hard drives, USB (universal serial bus) drives, or any other machine readable storage medium, wherein, when the computing device program code is loaded into and executed by a computing device, the computing device becomes an apparatus for practicing implementations of the disclosure. Implementations also may be implemented in the form of computing device program code, for example, whether stored in a storage medium, loaded into and/or executed by a computing device, or transmitted over some transmission medium, such as over electrical wiring or cabling, through fiber optics, or via electromagnetic radiation, wherein when the computing device program code is loaded into and executed by a computing device, the computing device becomes an apparatus for practicing implementations of the disclosure. When implemented on a general-purpose microprocessor, the computing device program code segments may configure the microprocessor to create specific logic circuits. In some configurations, a set of computing device-readable instructions stored on a computing device-readable storage medium may be implemented by a general-purpose processor, which may transform the general-purpose processor or a device containing the general-purpose processor into a special-purpose device configured to implement or carry out the instructions. Implementations may be implemented using hardware that may include a processor, such as a general-purpose microprocessor and/or an Application Specific Integrated Circuit (ASIC) that implements all or part of the techniques according to implementations of the disclosure in hardware and/or firmware. The processor may be coupled to memory, such as RAM, ROM, flash memory, a hard disk or any other device capable of storing electronic information. The memory may store instructions adapted to be executed by the processor to perform the techniques according to implementations of the disclosure.

The foregoing description, for purpose of explanation, has been described with reference to specific implementations.

However, the illustrative discussions above are not intended to be exhaustive or to limit implementations of the disclosure to the precise forms disclosed. Many modifications and variations are possible in view of the above teachings. The implementations were chosen and described in order to explain the principles of implementations of the disclosure and their practical applications, to thereby enable others skilled in the art to utilize those implementations as well as various implementations with various modifications as may be suited to the particular use contemplated.

The invention claimed is:

1. A system comprising:
an electrode;
a computing device comprising a processor in communication with the electrode; and
a non-transitory, computer-readable medium in communication with the processor and storing instructions that, when executed by the processor, cause the processor to perform operations comprising:
a sequence of stimuli comprised of a stimulus element or a plurality of stimulus elements:
a set of sequences of stimuli:
presenting a first sequence of stimuli to: (i) a first set of subjects associated with a first selection criteria and (ii) a second set of subjects associated with a second selection criteria;
detecting a first set of voltage fluctuation sequences, the first set of voltage fluctuation sequences comprising a sequence of voltage fluctuations from each of the first set of subjects;
detecting a second set of voltage fluctuation sequences, the second set of voltage fluctuation sequences comprising a sequence of voltage fluctuations from each of the second set of subjects;
determining, by a neural network, a pattern of voltage fluctuations characteristic of the first set of voltage fluctuation sequences and not characteristic of the second set voltage fluctuation sequences;
providing a recommendation for a selection of subjects from among a third set of subjects based on the pattern of voltage fluctuations;
presenting, by the sensory presentation device, the set of sequences of stimuli to the first set of subjects;
determining, by the neural network, a respective correlation value for each of the set of sequences of stimuli,
selecting, by the first computing device, the first sequence of stimuli from among the set of sequences of stimuli based on the respective correlation value for the first sequence of stimuli, presenting a first sequence of stimuli to: (i) a fourth set of subjects associated with a fourth selection criteria and (ii) said second set of subjects associated with a fourth selection criteria;
detecting a fourth set of voltage fluctuation sequences, the fourth set of voltage fluctuation sequences comprising a sequence of voltage fluctuations from each of the fourth set of subjects;
presenting said second set of voltage fluctuation sequences, the second set of voltage fluctuation sequences comprising a sequence of voltage fluctuations from each of said second set of subjects;
determining, by a neural network, a pattern of voltage fluctuations characteristic of the fourth set of voltage fluctuation sequences and not characteristic of the second set voltage fluctuation sequences;
providing a recommendation for a selection of subjects from among a further set of subjects based on the pattern of voltage fluctuations;
presenting, by the sensory presentation device, a set of sequences of stimuli to the fourth set of subjects;
determining, by the neural network, a respective correlation value for each of the set of sequences of stimuli,
selecting, by the fourth computing device, the fourth sequence of stimuli from among the set of sequences of stimuli based on the respective correlation value for the fourth sequence of stimuli.

2. The system of claim 1 repeating N times to compare the candidate group referred to as the second group, with new desired group signatures determine the best correlation by presenting said second set of voltage fluctuation sequences, the second set of voltage fluctuation sequences comprising a sequence of voltage fluctuations from each of said second set of subjects;
determining, by a neural network, a pattern of voltage fluctuations characteristic of the fourth set of voltage fluctuation sequences and not characteristic of the second set voltage fluctuation sequences;
providing a recommendation for a selection of subjects from among a N set of subjects based on the pattern of voltage fluctuations.

3. The system of claim 1 wherein some of the stimulus elements of a sequence of stimuli are selected for replacement or modification according to the respective correlation value for each of the set sequences of stimuli to maximize the respective correlation value.

4. The system of claim 1, wherein the sequence of stimuli or the set of sequence stimuli is standardized for more than one selection criteria for test subjects.

5. The system of claim 1 wherein a template comprising a digital reference of distinctive characteristics extracted from the patterns of voltage fluctuations for sets of test subjects characterized by common selection criteria is stored in the computer.

6. The system of claim 1 wherein a template comprising a digital reference of distinctive characteristics extracted from the patterns of voltage fluctuations for test subjects is stored in the computer.

7. The system of claim 1 wherein templates of sets of test subjects characterized by common selection criteria and individual test subjects are compared to establish a match score related to the degree of similarity between the two templates.

* * * * *